United States Patent [19]

Pant

[11] Patent Number: 4,962,187
[45] Date of Patent: Oct. 9, 1990

[54] COMMON ANTIGEN FOR COLORECTAL AND MUCINOUS OVARIAN TUMORS AND PROCESS FOR ISOLATING THE SAME

[75] Inventor: Keshab D. Pant, Albuquerque, N. Mex.

[73] Assignee: Cota Biotech, Albuquerque, N. Mex.

[21] Appl. No.: 933,304

[22] Filed: Nov. 21, 1986

Related U.S. Application Data

[63] Continuation of Ser. No. 674,494, Nov. 28, 1984.

[51] Int. Cl.$^5$ .................... C07K 15/00; A61K 39/00
[52] U.S. Cl. .................... 530/350; 530/395; 530/387; 530/389; 530/827; 424/1.1; 424/85.8; 424/88; 424/551; 424/559; 436/544; 436/543; 436/545; 436/547
[58] Field of Search .................... 424/88, 85, 1.1, 95, 424/104, 105; 530/350, 395, 827, 387, 389; 435/68; 436/544, 543, 545, 547

[56] References Cited

U.S. PATENT DOCUMENTS

| | | | |
|---|---|---|---|
| 3,697,638 | 10/1972 | Hansen | 424/88 |
| 4,273,537 | 10/1981 | Wong | 424/1.1 |
| 4,293,537 | 10/1981 | Wong | 424/1.1 |
| 4,468,457 | 8/1984 | Goldenberg et al. | 424/88 |
| 4,489,167 | 12/1984 | Ochi et al. | 260/112 R |

OTHER PUBLICATIONS

Pant et al *Tumor Biology* 5(5) 1984, pp. 243–254.
Ma et al. *Pathology* 15(4) 1983, pp. 385–391.
Pant et al *Nucl Med Biol* 100, 1987 pp. 1–9.
CA #24283r Thomson et al (vol. 93).
CA #83567x Jeny et al (vol. 100).
Pant, "Advances in Cancer Research", XI Annual Meeting, Stockholm, Sweden, Sep. 11–15, 1983, p. 25.
Thomson, *Eur. J. Cancer*, 16(4), 539–51 (Eng) 1980.

*Primary Examiner*—Garnette D. Draper
*Attorney, Agent, or Firm*—Berman, Aisenberg & Platt

[57] ABSTRACT

A purified common antigen for colorectal and mucinous ovarian cancer (COTA) is provided which is antigenically distinct from CSAp, CEA and Ca 19-9. The COTA antigen is useful for producing a COTA antibody which is nonreactive with CSAp, CEA or Ca 19-9.

10 Claims, No Drawings

COMMON ANTIGEN FOR COLORECTAL AND MUCINOUS OVARIAN TUMORS AND PROCESS FOR ISOLATING THE SAME

This application is a continuation of Ser. No. 674,494, filed Nov. 23, 1984.

BACKGROUND OF THE INVENTION

This invention relates to identification of a new common antigen of colorectal and mucinous ovarian tumors (COTA) and to a process for isolating the same. This invention also relates to clinical application of COTA and anti-COTA antibodies in detection and diagnosis of colorectal and ovarian tumors.

Presently, known and well studied antigens associated with colon cancer include CSAp, CEA and Ca 19-9. The term CEA is conventionally recognized as representing "Carcimoembryonic antigen" which was originally described as being present in intodermal derived tumors of the gastrointestinal tract [Gold et al., J. Exp. Med. 121:439–462 (1965)]. The term CSAp is conventionally recognized as representing "colon specific antigen (protein)" which was originally described as a colon cancer associated antigen and subsequently detected in some ovarian cancers [Pant et al., Immun. Comm. 6:411–421 (1977)]. The term Ca 19-9 is conventionally recognized as representing "Carbohydrate antigen 19-9" and was originally found as a colorectal carcinoma-specific antigen [Koprowski et al., Somatic Cell Genetics 5:957–972 (1979)]. It is not practical to diagnose colorectal cancers by assaying for CSAp, since CSAp is only elevated in the plasma of about 61% of advanced colorectal cancer patients. Also, the assay for CEA in diagnosis of colorectal cancers is not definitive since CEA is an antigen marker for a wide variety of cancers, only one of which is colon cancer. Similarly, the diagnosis of colorectal cancer based on Ca 19-9 assay is not definitive as Ca 19-9 is elevated in greater percentage in the plasma of pancreatic cancer patients and is elevated in only about 58% of advanced untreated colorectal cancer patients.

Reference to mucins in the neoplasms of colon have suggested chemical and immunological differences between normal and neoplastic colonic mucoproteins (Gold et al, Nature 255, 85–87) (1975). Unfortunately, these studies which describe a normal and tumor derived mucoprotein antigen designated CMA were conducted with unabsorbed xenogenic antiserum and require substantial validation with application of more specific antibodies before a definitive statement can be made on tumor specificity of tumor derived CMA. It has been observed that an antiserum to mucin isolated from benign mucinous cytadenomas from human ovaries has antigenic reactivity towards mucosal extracts of colorectal cancers, although was absent in extracts from normal tissue and tumors of the ovaries, stomach, lung and breast. (McNeil et al, Cancer Res. 29, 1535–1540). McNeil et al postulated that ovarian mucin contained antigenic material common to "altered" mucin found in colon cancer tissue. In another report (Narin et al, Brit. J. Cancer 25, 276–279) an antigen common to normal colon and ovarian cystadenoma was described leading authors to conclude that ovarian mucinous cystadenomas were derived from multipotent intestinal cells and could arise by unilateral intestinal development of a teratoma.

A composition containing a common antigen for malignant human colorectal and mucinous ovarian tumors has been disclosed by Pant et al at the Oncodevelopmental Biology and Medicine XI annual meeting, Stockholm, Sweden (1983). This antigen was obtained by first forming an antibody against human colon cancer tissue extract by immunizing a goat with the extract. The goat sera containing the antibodies was absorbed with extracts of human tissues, plasma and with CEA. The resultant antiserum contained the antibody to colorectal and ovarian tumor antigen (COTA). However, the COTA antibody containing serum was not purified further.

Although the anti-COTA antibodies were specific for COTA, the antiserum also contained an excess of dissolved normal tissue antigens, normal plasma, and CEA.

In order to prepare specific anti-COTA antibodies without having dissolved normal antigens, plasma and CEA in it, goat serum containing anti-COTA antibodies was first precipitated by conventional 50% and then by 33% ammonium sulfate method. The immunoglobulins (after dissolving and dialysis in phosphate buffered saline) were concentrated to half the original volume. The preparation was then passed through an affinity column (cyanogen bromide activated Sepharose 4B) made of a mixture of normal human colon, lung, liver, spleen, kidney and plasma. The unadsorbed material was concentrated to half the original volume and then passed through an affinity support made of CEA. The unadsorbed material was concentrated to give a concentration of 2 mg/ml solution and contained specific anti-COTA reactivity.

In order to recover COTA, colon cancer homogenate and/or mucinous ovarian cyst fluid was fractionated on Sephadex G-200. COTA appeared in the void volume from Sephadex G-200 column. This material containing COTA was further fractionated on Sepharose 4B column wherefrom COTA was eluted at 3–6 million molecular weight fraction. This COTA preparation was not adequately pure so that it could be used to raise specific anti-COTA antibodies in the animals since the preparation still contained other tissue antigens present in the original colon cancer homogenate or in the mucinous ovarian cyst fluid.

Accordingly, it would be highly desirable to provide a means for obtaining a COTA which is pure so that it could be utilized to produce specific antibodies to COTA. These antibodies, in turn, could be utilized to recover more highly purified COTA and could be used in development of diagnostic tests for detection and diagnosis of colorectal and ovarian cancers. Presently available COTA is not sufficiently pure for raising specific anti-COTA antibodies nor the antibodies are without dissolved normal tissue antigens, plasma and CEA so as to render them useful to correspondingly recover COTA or to utilize them in development of reliable diagnostic tests.

SUMMARY OF THE INVENTION

The present invention provides highly purified antigen to human colorectal and mucinous ovarian tumors (COTA) and highly purified antibodies to COTA. COTA antigen is found in malignant colorectal tumors, mucinous ovarian tumors and in mucinous ovarian cystadenocarcinoma cyst fluids. Tumor tissue extracts or the mucinous cyst fluids are treated with DEAE ion exchange resin in order to bind anionic proteins and glycoproteins to the resin. The ion-exchange resin is eluted with sodium chloride solution at varying molar strengths and the fraction eluted between 0.3 M and 0.5 M molar strength of sodium chloride is recovered and contains the COTA. The recovered eluted fraction then is passed through a Sepharose 4B column adapted to separate proteins and glycoproteins by molecular weight. The fraction collected from the Sepharose 4B column having a molecular weight between about 3 and about 15 million is recovered. Since COTA is mucin in character, such large distribution in molecular size is expected. The purified COTA then can be utilized to produce antibodies to COTA. COTA is administered to a non-human animal and after a series of immunization, the serum containing the antibody to COTA is recovered. The serum is then processed to isolate specific immunoglobulins by ammonium sulfate precipitation followed by adsorption of antibodies to a mixture of affinity immunoadsorbants made of normal human colon and other normal tissues, plasma and CEA to remove antibodies which would interfere with the antibodies to COTA. The purified antiserum containing antibodies to COTA that is free of other contaminating antibodies and retains immunoreactivity to COTA present in colorectal and mucinous ovarian cyst fluids.

DESCRIPTION OF SPECIFIC EMBODIMENTS

The colon-ovary tumor antigen or COTA of this invention is found in malignant colorectal, mucinous ovarian tumors and in mucinous ovarian cystadenocarcinoma cyst fluids. COTA is distinct from other colon cancer associated antigens, such as CEA, CSAp and Ca 19-9. COTA is not present in normal colon, ovary, lung, liver, spleen and kidney tissues and in normal plasma. Furthermore, COTA antigen is not found in serous adenocarcinoma of the ovaries, extracts of adenocarcinoma of lung, breast, kidney or stomach. COTA is stable to heating at 65° C. for 5 minutes. COTA elutes from DEAE Sepharose ion exchange matrix with sodium chloride eluent having 0.3 molar to 0.5 molar NaCl. COTA migrates to the alpha-2 region in immunoelectrophoresis. COTA has a size of between 3 and 15 million daltons. COTA is present in goblet cell mucin of colorectal cancer tissue. COTA of this invention is derived from tissue extract of malignant colorectal tumors or mucinous ovarian tumors or from mucinous ovarian cystadenocarcinoma cyst fluids. The extract obtained after homogenization and high speed centrifugation of colon cancer tissue or mucinous cyst fluid containing COTA is treated with diethyl aminoethyl Sepharose or diethyl aminoethyl cellulose (DEAE). The anionic proteins and glycoproteins from the tumor tissue extract or from mucinous ovarian cyst fluid become bound to the resin. The bound proteins and glycoproteins then are eluted with aqueous solution of sodium chloride of varying normality. It has been found that the fraction containing COTA is totally eluted from the column at a sodium chloride molarity of between about 0.2 and about 1.0, preferably between about 0.3 and about 0.5. The eluted fraction containing COTA then is equilibrated with phosphate buffered saline and is concentrated by filtration through a filter which retains molecules having a molecular size of 30,000 daltons (PM-30) or greater.

COTA obtained by DEAE treatment and concentrated by PM-30 membrane filtration is further purified by fractionation on Sepharose 4B column to recover the fractions having a molecular size between about 3-15 million daltons. It has been found that the active COTA antigen is comprised of a plurality of molecules within 3 to 15 million dalton range.

In order to produce the antibodies to COTA, it is administered to a non-human animal by conventional means and after repeated immunization for about 10 weeks, the animal is bled and the serum is recovered. The animal is bled two weeks after the last injection.

The serum then is precipitated by conventional 50% and 33% ammonium sulfate saturation method and immunoglobulins (IgG) are separated. The immunoglobulins are then adsorbed on an affinity immunoadsorbent column made of a mixture of normal human colon and other human tissues, normal human plasma and CEA in order to remove antibodies to the antigens contained in the human tissues and human plasma as well as the CEA. The unadsorbed immunoglobulins are eluted from the affinity column and then concentrated by PM-30 filtration and contain the antibodies to COTA.

In an alternate method, the serum is absorbed with the addition of normal human tissues, normal human plasma and CEA in order to remove antibodies to the antigens contained in the human tissues, plasma and for CEA. The mixture is incubated at 37° C. for 1 hour and the agglutinated products then are separated by centrifugation and the supernatant containing the antibody to COTA is recovered. An affinity immunoadsorbent is prepared by binding the COTA to cyanogen-bromide-activated Sepharose 4B or to N-succinimide esters of a derivatized crosslinked agarose gel bead support. The binding of antigens through crosslinking cyclic and acyclic imidocarbonates produced by cyanogen bromide or by replacement of N-succiimide esters is effected by conventional means well known in the art. The serum containing the antibody to COTA then is passed through the column containing the bound COTA so that the specific anti-COTA anti-bodies interact with bound COTA and are retained on the column. Subsequently, the antibody is eluted from the column by passing 3 molar ammonium thiocyanate through the column to free and recover the antibody.

It has been found that the COTA obtained by the process of this invention is far purer than that previously obtained and therefore the antibody to the COTA produced with the antigen is far purer than previously obtained.

As set forth above, the COTA is useful for producing and isolating the antibody to the COTA. The antibody to COTA can be tagged by any conventional tag, such as a radioactive molecule, such as 99m technetium, 125 iodine or 131 iodine, so that it can be used in conventional diagnostic procedures by detection of COTA in colorectal and ovarian cancer patients. Furthermore, the antibody can be tagged with an enzyme to render the tagged antibody useful in conventional diagnostic tests based on ELISA or the antibody can be tagged with a fluorescent molecule, such as fluorescein isothiocyanate or rhodamine, so that the tagged antibody can be used in conventional fluorescent analysis.

The following examples illustrate the present invention and are not intended to limit the same.

EXAMPLE I

Labeling of anti-COTA antibodies with $^{125}$Iodine or $^{131}$Iodine is accomplished by the method of Greenwood, Hunter and Glover, (Biochem J. 1963) and labeling of anti-COTA antibodies with Technetium-99m is carried out by pretinning method of Rhodes et al.

$^{99m}$Tc-Labeling and Acceptance Testing of Radiolabeled Antibodies and Antibody Fragments", in *Tumor Imagining*, Buchiel and Rhodes editors, Masson Publishing, New York (1982) which is as follows:

A solution containing 40 mm potassium hydrogen phthalate and 10 mm potassium sodium tartrate was made in distilled water. To 20 ml of phthalate-tartrate solution, 0.2 ml of 0.5 m SnCl$_2$ solution (prepared in conc. HCl) was added. The pH of the resultant mixture is brought to 5.6 by 10 N NaOH. To 3.2 ml of phthalate-tartrate SnCl$_2$ solution, 0.5 ml of normal goat IgG or anti-COTA antibody containing 5 mg of protein in normal saline is added and sealed. The mixture is allowed to react at the room temperature for 21 hours. To 0.32 ml of this mixture, 0.3 ml of TcO$_4$ (1 millicurie) is added and allowed to react for 30 minutes in a stoppered tube. Remaining 0.32 ml aliquots of phthalate-tartrate SnCl$_2$ mixture are lyophilized and stored at 4° C. for future use.

A PD-10 (Sephadex G-25) column was equilibrated with phthalate-tartrate-SnCl$_2$ buffer and the same buffer is used to elute technetium labeled protein. The radiolabeled immunoglobulin obtained from the void of PD-10 fractionation was mixed with 0.5 ml of normal human plasma and incubated for 24 hours at room temperature. The mixture was then fractionated on Sephadex G-200 column using normal saline as elution buffer. This should that the tc-99m label did not exchange off the antibody.

Coupling of affinity purified anti-COTA antibodies to horseradish peroxidase (HRP) is carried out according to method of Engvall (J. Immunol. 1972). The method is as follows:

10 mg of HRP (Sigma type VI) was dissolved in 0.2 ml of 1.25% technical grade glutaraldehyde, in PBS, pH 7.2, and will be left at room temperature for overnight. The reaction mixture will then be diluted to 1.0 ml and dialyzed against 0.1 M carbonate buffer, pH 9.2. Goat anti-COTA IgG (5 mg) in 0.25 ml of carbonate buffer will be then added to it and left for overnight at room temperature. Remaining reactive groups will be blocked by addition of 0.1 ml of 0.2 M lysine. The conjugate will be fractionated on Sephadex G-200 column and HRP conjugated fraction will be pooled and stored in cold.

For fluorescein labeling of anti-COTA antibodies, a 1 mg/ml solution of fluorescein isothiocyanate (FITC) was made in 0.1 M, M+9.0 carbonate-bicarbonate buffer. To 1 ml of 10 mg/ml solution of affinity purified anti-COTA antibodies, 0.1 ml of carbonate-bicarbonate buffer was added and the contents were placed at 4° C. To this mixture, 0.1 ml of 1 mg/ml solution of FITC was added. The pH of the mixture was readjusted to pH 9.0 by 0.1 N NaOH. The contents were stirred gently at 4° C. for overnight. Unreacted FITC were separated by gel filtration on Sephadex G-50. The conjugate was stored at 4° C. after addition of 0.1% sodium azide.

EXAMPLE II

Preparation and Purification of COTA: Specimens of colorectal cancer tissues and mucinous ovarian cyst fluids were obtained from surgery and autopsy cases. The tissues were weighed and then homogenized in 5 volumes of deionized water (w/v) by a polytron for 3-5 minutes under ice water. The tissue homogenates were then centrifuged at 48,000×g for 1 hour in Sorvall RC-5B (4° C.). The supernatants were collected and freeze dried. Similarly, samples of mucinous ovarian cyst fluids were also freeze dried. A 10% working solution of the freeze dried preparation was made for purification of COTA.

DEAE Purification of COTA: 25 ml of DEAE Sepharose CL-6B were equilibrated with 0.01 molar phosphate buffer, pH 7.2, and to it 25 ml of 10% solution of colon cancer extract or mucinous ovarian adenocarcinoma cyst fluid was added and mixed for 30 minutes. Elutions of DEAE were carried out by buchner filtration with 0.1, 0.3, 0.5, 1.0 and 2.0 molar sodium chloride made in 0.01 molar phosphate buffer, pH, 7.2. The eluted materials were equilibrated and concentrated by Amicon filtration (PM-30) to 5.0 ml and each fraction was tested by immunodiffusion for presence of COTA. It was found that COTA eluted between 0.3–0.5 molar sodium chloride concentration.

Sepharose 4B Chromatography: COTA obtained by DEAE method is further purified by fractionation on Sepharose 4B gel. A column (2.6×90 cm) is packed with Sepharose 4B and equilibrated with phosphate buffered saline. The column is calibrated with molecular weight markers thyroglobulin, bovine serum albumin and adolase. 5 ml COTA obtained by DEAE procedure (usually 3–5 mg protein per ml) is fractionated on Sepharose 4B and the material eluting immediately after void is collected and concentrated by Amicon PM-30 filtration to the original volume and contains COTA.

Immunization of Goats and Preparation of Anti-COTA Antibodies: Goats were immunized at two week intervals with 1 ml of purified COTA (1.3 mg/ml protein) mixed in Freund's adjuvant and given subcutaneously. The first injection was made in 1 ml of complete Freund's adjuvant and subsequent immunizations were made in incomplete Freund's adjuvant. The goats received a total of four injections and were bled after 15 days from the last injection from jugular vein.

Goat anti-COTA antiserum is precipitated with 50% and then 33% saturation of ammonium sulfate. The precipitate is dissolved in phosphate buffered saline pH 7.2 (PBS) to the original volume and dialyzed against PBS for 48 hours with several changes of the buffer. The immunoglobulin preparation is further concentrated to half the original volume and aliquots of it are passed through an affinity column made of mixture of normal human colon, lung, liver, spleen, kidney and plasma. The material is eluted with PBS and unadsorbed fraction is collected and concentrated on PM-30 membrane to original volume. This immunoglobulin preparation is further passed through a CEA affinity column and the unadsorbed fraction is collected and concentrated by Amicon PM-30 filtration to give approximately 2 mg/ml solution. This preparation contained purified specific anti-COTA antibodies.

Characterization of COTA

Double Immunodiffusion: A 1% agar solution was prepared in a buffer composed of a 1:3 mixture of barbital buffer (Beckman immunoelectrophoresis buffer pH 8.6, ionic strength, 0.075) and water.

The agar solution was heated to solubilize the agar and a thin layer of the solution coated onto slides. The slides, with the appropriate additions of reagents to each of the respective wells, were incubated for 24 hours at room temperature and then soaked in PBS for an additional 72 hours. The slides were rinsed in deionized water for 24 hours and air dried. The precipitate bands were visualized after staining with a 7% acetic acid. The bands couldn't be perceived without staining.

Immunoelectrophoresis: Immunoelectrophoresis of COTA was performed on a Bio-Rad electrophoresis apparatus with Beckman barbital buffer, pH 8.6 (ionic strength, 0.075) and using 5 ma current at 220 V for 50 minutes. The outer trough was then filled with anti-COTA-antibodies and the slide was incubated in a humid chamber for 24 hours. The slide was washed in PBS for 24 hours and rinsed in deionized water for 24 hours, air dried and stained with 1% amido black in 7% acetic acid and then destained with 7% acetic acid.

Heat Stability of COTA: A 50 mg/ml solution of mucinous ovarian adenocarcinoma cyst fluid was heated in a water bath at 65° C. for 5 minutes. The heated material was tested for immunoreactivity against anti-COTA antibodies in the immunodiffusion.

Indirect Immunofluorescent Staining for COTA: Histologic sections of colon cancer tissue 4–5 μ in thickness were deparaffinized and hydrated in PBS. One set of sections was reacted with 1:8 dilution of goat anti-COTA antibodies. The other set of slides was reacted with 1:8 dilution of goat anti-COTA antibodies which were further absorbed with lyophilized mucinous ovarian adenocarcinoma cyst fluid to remove anti-COTA reactivity and serve as control. The sections were then reacted with 1:200 dilution of fluorescein conjugated rabbit anti-goat antibody and incubated at room temperature for 30 minutes and then washed with PBS for 30 minutes with several changes of buffer. The sections were mounted and examined using a epifluorescence microscope.

CEA and Anti-CEA Antibodies: CEA was extracted from a pool of colon cancer tissue homogenates (1:5 w/v). The homogenate was treated with equal volume of 1.2 m perchloric acid and the mixture was stirred for 30 minutes at 4° C. and then centrifuged at 2,000 rpm at 4° C. for 15 minutes. The supernatant was collected and dialyzed against distilled water for 24 hours and centrifuged at 2,000 rpm for 15 minutes to remove insoluble material. The clear supernatant was concentrated by Amicon PM-30 filtration and fractionated on Sephadex G-200 with PBS. The material eluting after void (180,000 mw) was collected and concentrated on Amicon PM-30 filtration to 1/20th of the original homogenate volume. Anti-CEA antibodies (rabbit) were obtained from Dakopatts, Calif. CEA reactivity of the preparation was tested in the immunodiffusion against Dako-anti-CEA as well as against in house goat anti-CEA preparation.

Anti-CSAp antibodies were isolated from 10 ml of serum of goat immunized with colon cancer homogenates. The goat antiserum was heat inactivated at 65° C. for 45 minutes and then absorbed with washed human AB+. The antibodies were precipitated with ammonium sulfate first at 50% saturation and after dissolving the precipitate in deionized water, at 33% saturation. After collecting the precipitate by centrifugation, the precipitate was dissolved in 5 ml of deionized water and dialyzed against PBS. The preparation was then reacted with a mixture of immunoadsorbents made of 100 mg each of normal human lung, liver, spleen, kidney and plasma conjugated to cyanogen bromide activated Sepharose 4B. The unabsorbed antibodies were concentrated on Amicon PM-30 and then allowed to react with immunoadsorbent column made of normal human colon mucosa. The unadsorbed antibodies were collected and concentrated on Amicon PM-30 membrane to approximately 1 mg/ml protein concentration and contained anti-CEA and anti-COTA antibodies. The adsorbed anti-CSAp antibodies were eluted with 3 M ammonium thiocyanate (in PBS). The anti-CSAp preparation was dialyzed against PBS and concentrated on PM-30 membrane to a protein concentration of 1 mg/ml.

Assay for CEA and Ca 19-9: CEA was assayed by Abbott ELISA method and Ca 19-9 by radioimmunoassay method supplied by centocor. Briefly, the method for assay of 19-9 is as follows: Polystyrene beads coated with mouse monoclonal antibody to CA 19-9 are incubated with serum specimen and appropriate standard and control. CA 19-9 present in the specimen are bound to the solid phase. Unbound materials present in the specimen are removed by aspiration of the fluid and washing of the beads. The same monoclonal anti-19-9 antibody labeled with $^{125}$I is incubated with the beads and, if CA 19-9 is present in the specimen, the radiolabeled anti-CA 19-9 is bound to the CA 19-9 antigen on the beads. Unbound labeled antibody is removed by aspiration. The bound radioactivity is determined by counting the beads in a gamma scintillation counter. The bound radioactivity is proportional to the concentration of the CA 19-9 in the specimen within the working range of the assay. A standard curve is obtained by plotting the CA 19-9 concentration of the standards versus bound radioactivity. The CA 19-9 concentration of the unknowns and control, run together with standards, can be determined from the standard curve.

Results

A 150 mg/ml solution of lyophilized extracts of malignant and normal tissues and ovarian adenocarcinoma cyst fluids were tested by immunodiffusion against anti-COTA antiserum (Table I). The results showed that of the malignant tissue extracts, 9/9 colon cancers, 2/2 mucinous ovarian cyst adenocarcinomas and 5/5 mucinous ovarian adenocarcinoma cyst fluids were positive while 5 serous ovarian adenocarcinoma tissue extracts and 5 serous adenocarcinoma cyst fluids and extracts of 4 lungs, 5 breasts, 3 kidneys and 1 stomach were negative. Among the normal tissues, 7 colons, 8 lungs, 7 livers, 7 spleens, 8 kidneys, 2 ovaries, 1 breast, 3 bladders and 5 plasma samples were negative.

CEA and Ca 19-9 determinations using anti-COTA antibodies, anti-CEA antibodies, and anti-Ca 19-9 antibodies respectively on mucinous and serous ovarian adenocarcinoma cyst fluids showed (Table II) that using the maximum amount considered normal of 2.5 mg/ml for CEA identification 5/5 mucinous cyst fluids and 3/5 serous cyst fluids were positive CEA. For Ca 19-9 identification using the maximum amount considered normal, with a cut off of 37 units per ml, 4/5 mucinous and 3/5 serous adenocarcinoma cyst fluids were positive for Ca 19-9 antigen. In contrast, COTA was separately identified in all the mucinous cyst fluids tested but not found in any of the serous cyst fluids tested, thus indicating no antigenic relaxtionship between COTA CEA and Ca 19-9. Units for CEA and Ca 19-9 are used as conventionally defined in the art and existing literature [CEA and Ca 19-9 test kits, Abbott Laboratories and Centocor Company; Koprowski et al., *Somatic Cell Genetics* 5:957–972 (1979); Pant et al., *Immun. Comm.* 6:411–421 (1977)]. The notations MO, FP etc. of Table II represent internal code labels for identification of the individual samples under test.

TABLE I

Immunodiffusion Reactivity of Malignant and Normal Tissue Extracts and Ovarian Cyst Fluids at 150 mg/ml Concentration

| Tissues | No. of Positive/Total |
|---|---|
| Malignant | |
| Colon | 9/9 |
| Ovary (Mucinous) | 2/2 |
| Ovary Cyst Fluid (Mucinous) | 5/5 |
| Ovary (Serous) | 0/4 |
| Ovary Cyst Fluid (Serous) | 0/5 |
| Lung | 0/4 |
| Breast | 0/5 |
| Kidney | 0/3 |
| Stomach | 0/1 |
| Normal | |
| Colon | 0/7 |
| Lung | 0/8 |
| Liver | 0/7 |
| Spleen | 0/7 |
| Kidney | 0/8 |
| Ovary | 0/2 |
| Breast | 0/1 |
| Bladder | 0/3 |
| Plasma | 0/5 |

TABLE II

Detection of COTA and Ca 19-9 in Ovarian Adenocarcinoma Cyst Fluids

| Ovarian Cyst Fluids | COTA I.D. at 150 mg/ml Conc. | CEA ng/ml | Ca 19-9 units/ml |
|---|---|---|---|
| Mucinous Type | | | |
| 1. Sample from patient 1 | + | 30.0 | 70.0 |
| 2. Sample from patient 2 | + | 30.0 | 120.0 |
| 3. Sample from patient 3 | + | 14.78 | 45.0 |
| 4. Sample from patient 4 | + | 30.0 | 4.0 |
| 5. Sample from patient 5 | + | 30.0 | 42.0 |
| Serous Type | | | |
| 1. Sample from patient 6 | − | 1.0 | 5 |
| 2. Sample from patient 7 | − | 1.9 | 45.0 |
| 3. Sample from patient 8 | − | 30.0 | 9.0 |
| 4. Sample from patient 9 | − | 3.3 | 120.0 |
| 5. Sample from patient 10 | − | 2.7 | 120.0 |

Specific immunoreactivity of anti-COTA antiserum to colon cancer extract and antigenic identity of COTA with ovarian mucinous adenocarcinoma cyst fluid and non-reactivity of CEA against anti-COTA antiserum has been demonstrated.

Anti-COTA antiserum reacted with mucinous ovarian adenocarcinoma cyst fluid at 150 mg/ml concentration while extracts of normal human lung, liver, spleen, kidney and plasma at same concentration were negative.

Individual immunoprecipition reaction of CEA and COTA and of CSAp and COTA were tested. A precipitin reaction between anti-CSAp and anti-COTA antiserum is due to presence of CSAp in anti-COTA antiserum as a result of absorption of antiserum with normal human colons.

DEAE treatment of mucinous ovarian adenocarcinoma cyst fluid and its elution with various sodium chloride concentration showed that COTA eluted between 0.2 molar–0.5 molar sodium chloride concentration.

Heating a 50 mg/ml solution of mucinous ovarian adenocarcinoma cyst fluid at 65° C. for 5 minutes retained COTA immunoreactivity. On immunoelectrophoresis of COTA preparation from colon cancer tissue extract and from mucinous ovarian adenocarcinoma cyst fluid, COTA migrated to alpha-2 region. Sephadex G-200 gel filtration of colon cancer extract and mucinous ovarian adenocarcinoma cyst fluid showed that COTA eluted in the void fraction. Further fractionation of the void material of Sepharose 4B, COTA activity appeared in 3–15 million size.

Indirect immunofluorescent staining of colon cancer tissue section showed that the antigen was located in the goblet cell mucin and absorption of anti-COTA antiserum by lyophilized mucinous ovarian adenocarcinoma cyst fluid removed the staining for COTA.

In the present study, an antigen designated COTA was demonstrated to be present in malignant colorectal tumors, mucinous ovarian tumors and in mucinous ovarian cystadenocarcinoma cyst fluids. COTA was found to be antigenically distinct from other colon cancer associated antigens CEA, CSAp and Ca 19-9. Of particular interest is the observation that COTA is not present in normal colon, ovary, lung, liver, spleen and kidney tissues and in normal plasma.

The results herein show that COTA is present in mucinous adenocarcinomas of the ovary and, although mucinous ovarian adenomas for COTA has not been examined, it is unlikely that COTA was detected after extensive absorption of the antiserum with several normal colon extracts, a procedure which would have removed the antigen studied by Narin et al. Similarly, COTA is not identical with the antigen described by McNeil et al as COTA is deleted in mucinous ovarian cystadenocarcinomas and cyst fluids derived from identical tumors. The recently observed cross reactivity of the monoclonal antibody Ca 19-9 (originally described to be associated with the carbohydrate moiety of a monosialoganglioside) with mucins in the plasma of cancer patients raises the question of whether COTA is identical to the determinant recognized by Ca 19-9. A mucinous cystadenocarcinoma cyst fluid which contained large amounts of COTA was negative for COTA while three of these were positive for Ca 19-9 shows that COTA is not identical to the antigen recognized by Ca 19-9.

Immunofluorescent staining of colorectal cancer tissue sections shows that COTA is present in goblet cells and is associated with the apical extracellular space. The staining patterns and the molecular weight of COTA 3–15 million daltons, shows that the antigen is a goblet cell mucin.

I claim:

1. A tumor identifying antigen (COTA) isolatable from and having specific binding affinity with human colorectal tumors and human ovarian tumors comprising at least one member selected from the group consisting of proteins and glycoproteins having a molecular weight of between 3 and 15 million daltons, said antigen being immunologically distinct from Carcinoembryonic antigen (CEA), Colon specific antigen p (CSAp), and Carbohydrate antigen 19-9 (Ca 19-9).

The term CEA is conventionally recognized as representing "Carcinoembryonic antigen" which was originally described as being present in intodermal derived tumors of the gastrointestinal tract [Gold et al., J. Exp. Med. 121:439–462 (1965]. The term CSAP is conventionally 2. An antigen of claim 1 free from other tissue, antigens, plasma and CEA.

3. An antigen (COTA) which
(a) is stable to heating at 65° C. for 5 minutes, (b) elutes from DEAE Sepharose ion exchange matrix with sodium chloride eluent, (c) migrates to the α-2 region in immunoelectrophoresis, (d) is present in goblet cell mucin of colorectal cancer tissue, (e) is isolatable from and has specific binding affinity with human colorectal tumors and human ovarian tumors, (f) is immunologically distinct from Carcinoembryonic antigen (CEA), Colon specific antigen p (CSAp), and Carbohydrate antigen 19-9 (Ca 19-9), (g) is not present in normal colon, ovary, lung, liver, spleen and kidney tissues, (h) is not present in normal plasma, and (i) is not found in serous adenocarcinoma of the ovaries or in extracts of adenocarcinoma of lung, breast, kidney or stomach.

4. An antigen of claim 3 having a purity sufficient to produce specific anti-COTA antibodies in animals.

5. Antiserum containing antibodies to the antigen of claim 8 which is free of contaminating antibodies and which retains immunoreactivity to COTA present in malignant colorectal tumors, in mucinous ovarian tumors or in mucinous ovarian cystadenocarcinoma cyst fluid.

6. An antibody specific for a tumor identifying antigen (COTA) of claim 1, said antibody being immunologically non-reactive with Carcinoembryonic antigen (CEA), Colon specific antigen p (CSAp), and Carbohydrate antigen 19-9 (Ca 19-9).

7. The specific antibody to the antigen of claim 8 being labeled with a radioactive molecule.

8. The specific antibody of claim 7 wherein the radioactive molecule is technetium 99m.

9. The specific antibody of claim 7 wherein the radioactive molecule is radioactive iodine.

10. A process for obtaining a tumor identifying antigen isolatable from and having specific binding affinity with human colorectal tumors and human ovarian tumors comprising the steps of:

passing a soluble extract obtained from at least one member selected from the group consisting of colorectal tumors, mucinous ovarian tumors and soluble cyst fluids into an ion exchange column;

eluting said column with aqueous sodium chloride solutions and recovering the eluate from said column which elutes between 0.3 and 0.5 molar sodium chloride solution; and fractionating said eluate by gel filtration to yield a fraction comprising proteins and glycoproteins having a molecular weight of between about 3 million and 15 million daltons.

* * * * *

UNITED STATES PATENT AND TRADEMARK OFFICE
CERTIFICATE OF CORRECTION

PATENT NO. : 4,962,187
DATED : October 9, 1990
INVENTOR(S) : PANT

It is certified that error appears in the above-identified patent and that said Letters Patent is hereby corrected as shown below:

Column 1, line 64, "colon." should read --colon--. Column 3, line 23, "that" should read --then--; line 44, Column 4, line 33, "N-succiimide" should read --N-succinimide--; line 39, "subsequently" should read --Subsequently--. Column 5, line 1, "$^{99m}$Tc-Labeling" should read --"Labeling--; line 3, "Imagining" should read --Imaging--; "Buchiel" should read --Burchiel--; line 28, "should" should read --shows--; "tc-99m" should read --Tc-99m--; line 36 "for over-" should read --over- --; line 40, "left for" should read --left--. Column 6, line 49, "PM-30" should read --Amicon PM-30--. Column 8, line 10, "centocor" should read --Centocor--; line 60, "relaxtionship" should read --relationship--; line 61, "CEA" should read --, CEA,--. Column 9, line 53, "immunoprecipition" should read --immunoprecipitin--. Column 10, line 35, "pa tients" should read --patients--; lines 58 to 64, "(Ca 19-9). ...CSAP is conventionally" should read --(Ca 19-9).--. Column 11, line 1, "exchangematrix" should read --exchange matrix--.

Signed and Sealed this

Twenty-ninth Day of September, 1992

Attest:

DOUGLAS B. COMER

Attesting Officer

Acting Commissioner of Patents and Trademarks